United States Patent [19]
Scheuer et al.

[11] Patent Number: 5,762,549
[45] Date of Patent: Jun. 9, 1998

[54] DEODORIZING OBJECT ATTACHABLE TO A VEHICULAR AUTOMOBILE VENTILATOR

[76] Inventors: Jean-Louis Scheuer, 22, rue de Siewiller, 67320 Drulingen; Marc Felten, 11 quai Koch, 67000 Strasbourge, both of France

[21] Appl. No.: 728,565

[22] Filed: Oct. 10, 1996

[30] Foreign Application Priority Data

Oct. 12, 1995 [FR] France ................................ 95 12191

[51] Int. Cl.⁶ .................................................. B60H 3/00
[52] U.S. Cl. .................................. 454/157; 422/124
[58] Field of Search ............................ 454/152, 155, 454/156, 157, 291, 328; 422/123, 124

[56] References Cited

U.S. PATENT DOCUMENTS 4,523,870  6/1985  Spector .
4,813,344  3/1989  Greif ................................... 454/157 X
4,840,773  6/1989  Wade .................................. 454/157 X
5,407,642  4/1995  Lord ......................................... 422/122
5,422,078  6/1995  Colon ................................. 422/124 X
5,527,493  6/1996  McElfresh et al. .................. 422/124 X

FOREIGN PATENT DOCUMENTS 0328702  2/1989  European Pat. Off. .
2263404  7/1993  United Kingdom .

*Primary Examiner*—Harold Joyce
*Attorney, Agent, or Firm*—Young & Basile, PC

[57] ABSTRACT

A deodorizing object is made up of two parts, first, a flat case containing an absorbent material impregnated with a perfumed substance and pierced by holes permitting the diffusion of perfume, and second, a block projecting from the rear face of the case. The block is formed of easily compressible material for the purpose of being inserted between the slats of a ventilator.

7 Claims, 2 Drawing Sheets

DEODORIZING OBJECT ATTACHABLE TO A VEHICULAR AUTOMOBILE VENTILATOR

BACKGROUND OF THE INVENTION

One already knows of deodorizers that fit into automobile ventilation system and which are generally made of a case containing an absorbent material impregnated by a perfumed product, the case containing orifices that one can eventually open more or less to allow the diffusion of the perfume, and presenting in its rear face parallel brackets, more or less flexibly designed to permit gripping of the slats of a ventilator, the whole case being made of molded plastic material.

The principal inconvenience of these deodorizers is that they are not adaptable to all ventilators on the market. In effect, the openings of these brackets are fixed and, if the attachment is possible based on the elasticity of the brackets then their spread is not as important in comparison to the thickness of the slats. It is otherwise (when the brackets are not fixed) when the spread is very important.

The present invention has as its goal to remedy this inconvenience by proposing a deodorizing object attachable to all existing ventilators, all the while costing less to produce than prior existing deodorizers.

SUMMARY OF THE INVENTION

The present invention is characterized essentially by two parts: first, a flat case containing an absorbent material impregnated with a perfumed substance, the case pierced by holes permitting the diffusion of perfume and, second, a block projecting from the rear face of the case, the block formed of easily compressible material for the purpose of being inserted between the slats of a ventilator.

An additional characteristic of the above-mentioned invention is that the free end of the block of compressible material contains at least one horizontal slit, perpendicular to the face of the case to which the block is mounted.

BRIEF DESCRIPTION OF THE DRAWINGS

The advantages and the characteristics of the above-mentioned invention will stand out more clearly in the following description which corresponds to the attached drawings wherein.

DESCRIPTION OF THE PREFERRED EMBODIMENT

Figure 1:
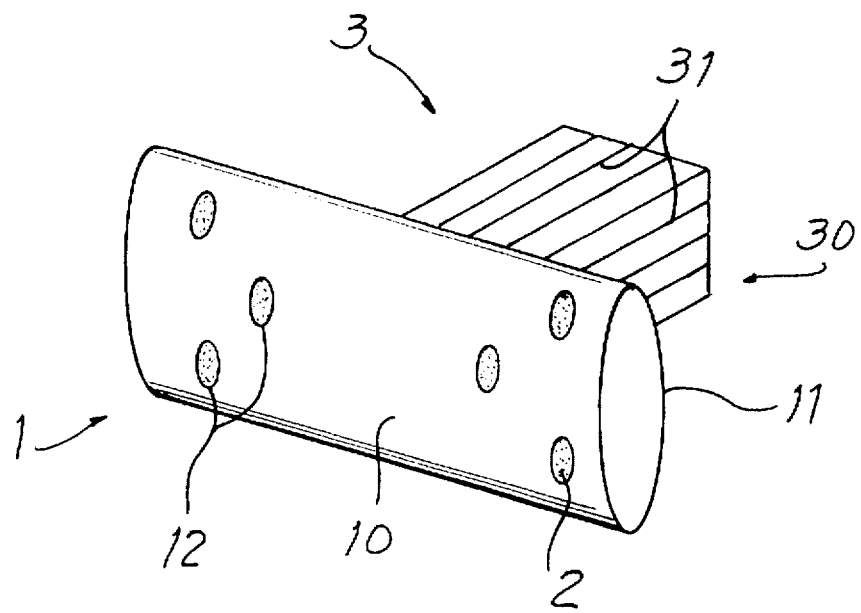
FIG. 1 represents a front view of the above-mentioned invention.
Figure 2:
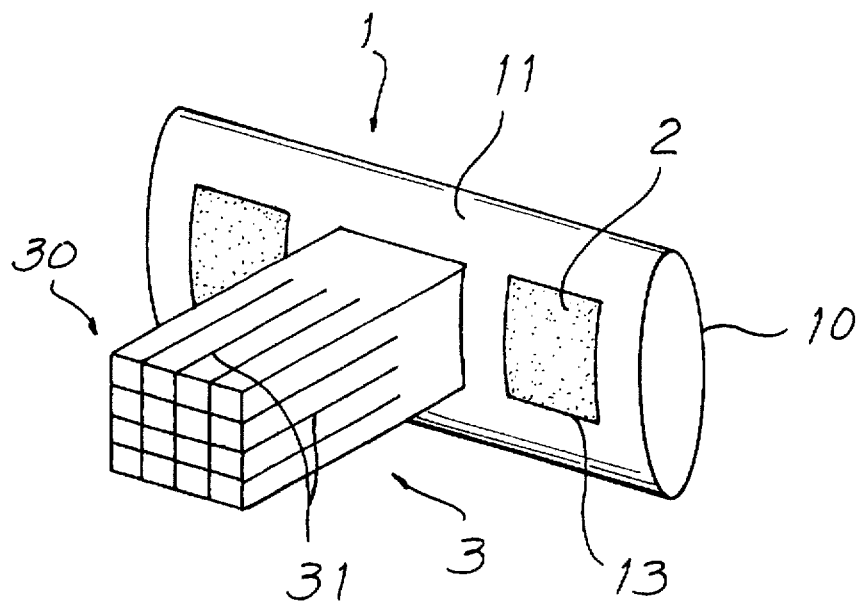
FIG. 2 represents a rear view of the same invention.

If one refers to these figures, one can see that the present invention is made up of a flat, rectangular case 1 containing an absorbent material 2 imbibed with a perfumed product, of which case 1 has a front face 10 and a rear face 11 each contain one or more apertures 12 and 13 respectively, permitting the diffusion of the perfume therethrough.

The case 1 is made of a semi-rigid type of plastic or cardboard material.

From the rear face 11, a block 3 projects perpendicularly. The block 3, which is a three-dimensional rectangle, is made of a flexible, compressible material of a foam plastic type.

The compressibility of the block 3 permits its introduction between two slats of a ventilator, while its expansion beyond the slats permits mounting which is largely sufficient to hold the light weight of the case 1.

Figure 3:
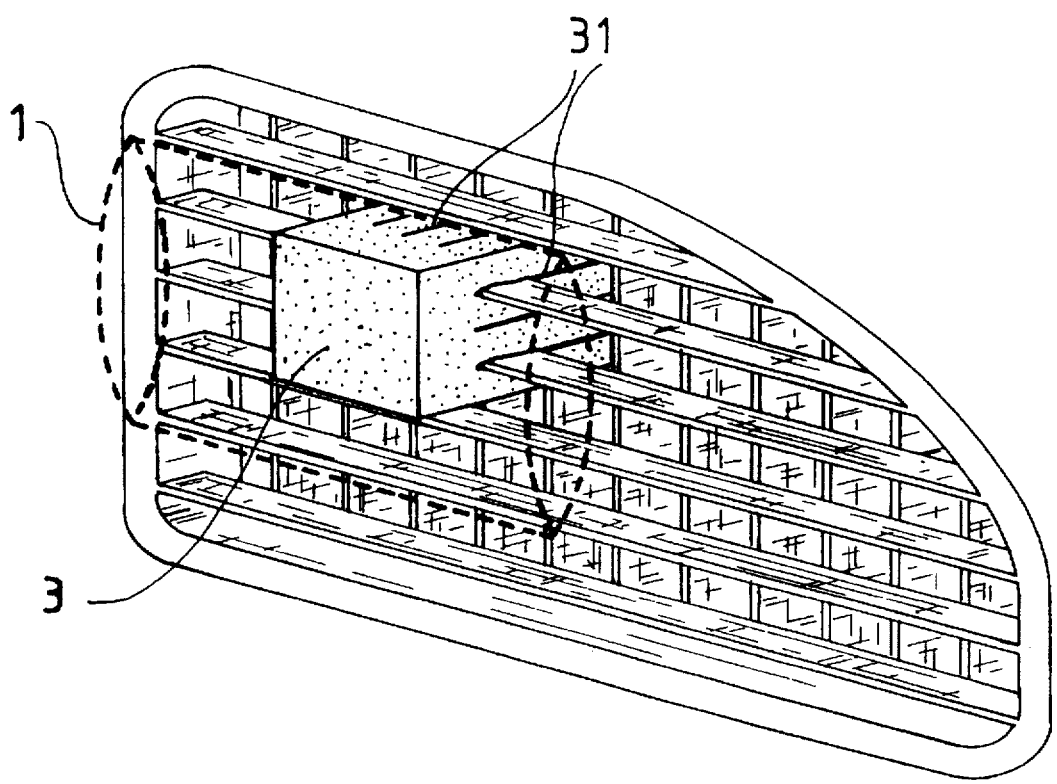
FIG. 3 represents a perspective view showing the mounting of the inventive deodorizer in a ventilator.

A free end 30 of the block 3 contains horizontal slits 31 allowing the affixation of the free end 30 to the ventilator by introducing one of the slats of the ventilator into one of the slits 31, the mounting being secured by pinching as shown in FIG. 3.

The use of this type of mounting is reserved mainly for ventilators of which the slats are very close together and/or very far apart.

The above-mentioned block 3 can therefore be easily mounted on the protective grill of a ventilator which is generally made up of intertwining metallic threads.

It is evident that while the above-mentioned invention is limited to the preceding description in regards to its realization, it is capable of supporting a number of modifications without changing the framework of the invention.

What is claimed is:

1. A deodorizer adaptable to a ventilator of an automobile, the ventilator having slats characterized by a flat case containing an absorbent material impregnated with a perfumed product, the case including at least one aperture permitting the diffusion of the perfume from the case, and a block projecting from a rear face of the case, the block formed of easily compressible material introducible between the slats of a ventilator to retain the case in the ventilator.

2. The deodorizer of claim 1 characterized by a free end of the block of compressible material containing at least one horizontal slit perpendicular to the rear face of the case to which the block is mounted.

3. The deodorizer according to claim 1 further characterized by the case having opposed front and rear surfaces, the at least one aperture including at least one aperture in each of the front and rear surfaces.

4. The deodorizer according to claim 1 further characterized by the ventilator having at least one pair of spaced slats, the block of compressible material introducible between the at least one pair of spaced slats and substantially filling a space between the pair of slats to engage the block and the case with the pair of slats.

5. The deodorizer according to claim 1 further characterized by the block having at least one vertical slit angularly disposed with respect to the horizontal slit.

6. A deodorizer adaptable to a ventilator of an automobile, the ventilator having slats, the deodorizer characterized by a flat case containing an absorbent material impregnated with a perfumed product, the case including at least one aperture permitting the diffusion of the perfume from the case, and a block protecting from a rear face of the case, the block formed of easily compressible foam plastic introducible between the slats of a ventilator.

7. A deodorizer adaptable to a ventilator of an automobile, the ventilator having slats, the deodorizer characterized by a flat case containing an absorbent material impregnated with a perfumed product, the case including at least one aperture permitting the diffusion of the perfume from the case, and a block protecting from a rear face of the case, the block formed of easily compressible foam plastic introducible between the slats of a ventilator, a free end of the block of compressible material containing at least one horizontal slit perpendicular to the rear face of the case to which the block is mounted.

* * * * *